(12) United States Patent
Pein

(10) Patent No.: US 6,290,670 B1
(45) Date of Patent: Sep. 18, 2001

(54) DEVICE FOR REMOVING PATHOLOGICAL CENTERS FOR USE IN HUMANS AND ANIMALS

(75) Inventor: Andreas Pein, Gross Grönau (DE)

(73) Assignee: Andreas Pein Medizintechnik GmbH, Schwerin (DE)

( * ) Notice: Subject to any disclaimer, the term of this patent is extended or adjusted under 35 U.S.C. 154(b) by 0 days.

(21) Appl. No.: 09/420,199

(22) Filed: Oct. 18, 1999

(30) Foreign Application Priority Data

Oct. 26, 1998 (EP) .............................................. 981 20 232

(51) Int. Cl.[7] .................................................... A61M 3/00
(52) U.S. Cl. .............................................. 604/43; 606/107
(58) Field of Search .................................. 604/19, 27, 35, 604/43, 48, 93, 118, 131, 264, 107

(56) References Cited

U.S. PATENT DOCUMENTS

| | | | |
|---|---|---|---|
| 3,882,872 | * 5/1975 | Douvas .................................. | 128/305 |
| 4,014,333 | 3/1977 | McIntyre ............................... | 128/240 |
| 4,024,866 | * 5/1977 | Wallach ................................ | 128/276 |
| 4,573,979 | 3/1986 | Blake .................................... | 604/240 |
| 5,322,504 | * 6/1994 | Doherty et al. ....................... | 606/167 |
| 5,403,323 | * 4/1995 | Smith .................................... | 606/107 |
| 5,733,256 | * 3/1998 | Costin ................................... | 604/22 |
| 5,788,667 | 8/1998 | Stoller .................................. | 604/22 |

FOREIGN PATENT DOCUMENTS

| | | | |
|---|---|---|---|
| 40 18 736 A1 | 6/1990 | (DE) .............................. | A61B/17/22 |
| 0 411 170 A1 | 2/1991 | (EP) .............................. | A61B/17/32 |
| 0 657 150 A1 | 6/1995 | (EP) .............................. | A61F/9/00 |
| 98/07398 | 2/1998 | (WO) .............................. | A61F/7/007 |

* cited by examiner

Primary Examiner—Sharon Kennedy
Assistant Examiner—Catherine Serke
(74) Attorney, Agent, or Firm—Darby & Darby

(57) ABSTRACT

A device for removing pathological centers is therefore proposed which consists of a supply capillary (11) with a supply channel (14), wherein the supply channel (14) has at its distal end a throttle and is operatively connected to the discharge channel (13) of the discharge capillary (12).

5 Claims, 1 Drawing Sheet

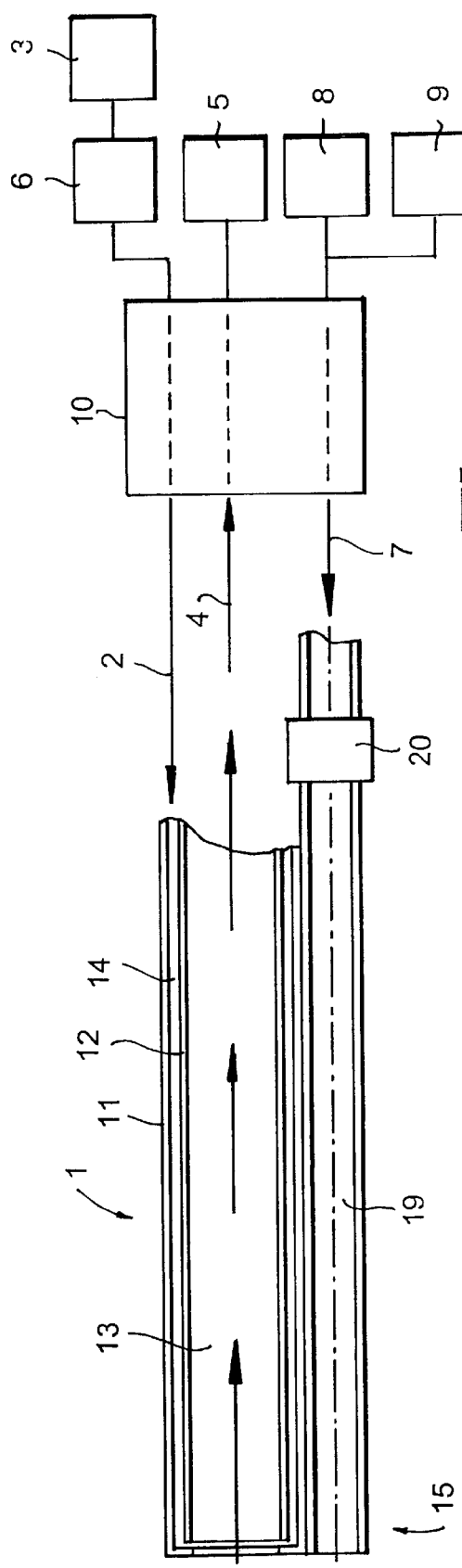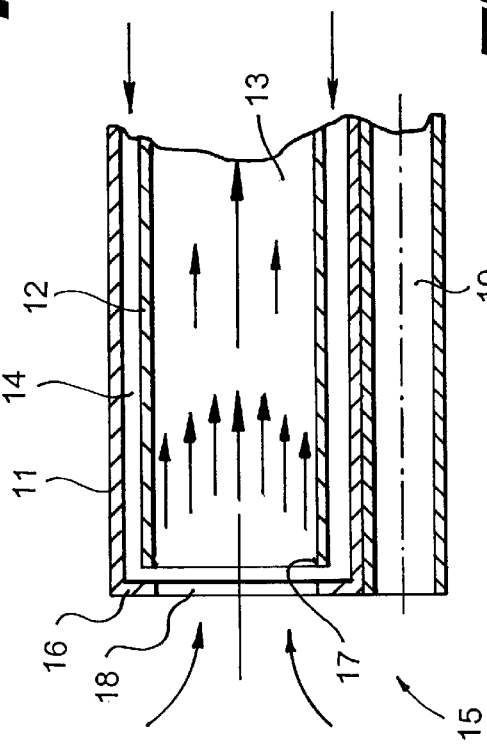

DEVICE FOR REMOVING PATHOLOGICAL CENTERS FOR USE IN HUMANS AND ANIMALS

BACKGROUND OF THE INVENTION

1. Field of the Invention

The present invention relates to a device for removing pathological centers useful for humans and animals. The device includes a supply capillary having a supply channel for a pressurized flow and a discharge capillary with a discharge channel, which is open to the pathological center, for suction flow.

Such devices are used in human and veterinary medicine, wherein pathological centers are understood as including bodily impairments and deficiencies in general.

2. Description of the Related Art

Pathological or etiological centers of the aforedescribed type can be found in the brain and in the central nervous system, including the eyes, and in those body structures which calls for a particularly mild form of invasive surgery due to the concentration of nerve and blood vessel tissue or other conditions. According to the present teachings, specialists treat or remove such pathological centers by surgical or micro-surgical means. These means are characterized by an applied force which is entirely or at least predominantly directed in a forward direction. These means include, for example, scalpels of any kind, coagulators and lasers of any kind, ultrasound aspirators, and the like. An pathological center or degenerative impairment of the aforedescribed type is, for example, a lens of the eye which may be impaired by a cataract and therefore may have to be removed and replaced by an artificial lens.

The first incision in the eye is a tunnel incision and the anterior capsule is opened with a flawless, preferably circular capsolorhexis. An instrument is then pushed into the diseased lens through this opening. The lens is then fractured, preferably by ultrasound, initially into small fragments which are subsequently suctioned off. After all fragments have been removed and the chamber of the eye has been cleaned, an artificial lens is inserted into the chamber of the eye through the channel of a special instrument. The lens relaxes when the instrument is pulled out and again assumes its original lens shape. Finally the artificial lens is oriented and secured in place.

Although this surgical procedure since has become routine, complications may still occur. For example, the residual fragments of the diseased lens can still not be completely removed from the chamber of the eye, since some of the peripheral fragments of the diseased cell residues are obscured from the view of the surgeon and may therefore remain in place. This creates a risk that the cataracts return. The cell residues can only be partially mobilized by manually injecting a fluid. In addition, the ultrasound energy produces excess heat which heats the corneal tissue and causes a loss of endothetical cells.

This surgical procedure also requires a variety of different surgical tools and a considerable number of independent time-consuming steps. This increases the cost of the surgical procedure. The large number of surgical steps and the large number of surgical tools also are demanding on the surgeon. As a result, the success of such a surgical procedure depends to a large extent on the surgeon's qualifications.

It is therefore an object of the invention to develop a method of the aforedescribed type which is less demanding on the surgeon, which can be performed in less time, and which is more gentle on the healthy tissue.

SUMMARY OF THE INVENTION

It is another object of the invention to provide a multi-functional device for carrying out the method.

The object is solved by providing a device for removing pathological centers which includes a supply capillary with a supply channel for a pressurized flow and a discharge capillary with a discharge channel, which is open to the pathological center, for a suction flow, the supply channel of the supply capillary has a throttle located at the distal end of the supply channel and is operatively connected with the discharge channel of the discharge capillary.

The invention eliminates the aforedescribed disadvantages of the present state of the art.

In addition, the method and the device have many applications and can be used at many locations where tissue has to be removed in order to be replaced or tested, independent if surgery is performed on the open body or in a body cavity. Advantageously, the surgical procedure is of high-quality and very gentle on healthy tissue. This is mainly due to the fact that with the method of the invention, the hydraulic jet no longer exerts a forward-directed force and therefore eliminates pressure build-up and possible turbulence in the body cavity. In particular, the retrograde effective direction of the hydraulic jet protects the healthy tissue. Furthermore, the volume of the removed tissue can be compensated which is advantageous with very small body cavities, for example in neurosurgery and ophthalmology.

As an additional advantage, the device is multi-functional and combines several functional elements. This protects the healthy tissue and simplifies and shortens the surgical procedure.

The invention will be described hereinafter in more detail with reference to an embodiment.

Other objects and features of the present invention will become apparent from the following detailed description considered in conjunction with the accompanying drawings. It is to be understood, however, that the drawings are intended solely for purposes of illustration and not as a definition of the limits of the invention, for which reference should be made to the appended claims.

BRIEF DESCRIPTION OF THE DRAWINGS

In the drawings, wherein like reference numerals delineate similar elements throughout the several views:

FIG. 1 is a schematically depiction of a simplified diagram of a hydro-jet device, and FIG. 2 is a schematically depiction of the hydro-membrane nozzle of the device.

DETAILED DESCRIPTION OF THE PRESENTLY PREFERRED EMBODIMENTS

Referring to FIG. 1, the hydro-jet device essentially includes a device 1 according to the invention for removing pathological centers. The device 1 is connected via a supply line 2 with a pressurized flow generator 3 and via a discharge line 4 with a reduced pressure flow generator 5. The pressurized flow generator 3 is associated with a pulse generator 6 which can be connected in addition. The device 1 also includes a second supply line 7 which is connected with a hydraulic pump 8 and with an auxiliary unit 9 which can be alternatively connected. The supply lines 2, 7 and the discharge line 4 pass through a control unit 10 which is operated manually by the surgeon.

The device 1 for removing pathological centers preferably consists, as indicated with particularity in FIG. 2, of an outer supply capillary 11 which is penetrated by an inner discharge capillary 12. The inner discharge capillary 12 includes a discharge channel 13 and is connected with the discharge line 4 of the reduced pressure flow generator 5. Both capillaries 11 and 12 are located on a common axis. Through proper selection of the inside diameter of the supply capillary 11 and of the outside diameter of the discharge capillary 12, an annular supply channel 14 with a defined unobstructed width is created which is connected to the supply line 2 of the pressurized flow generator 3. The defined unobstructed width is determined by the desired ratio between the cross-sectional surfaces of the annular supply channel 14 and the discharge channel 13 of the discharge capillary 12. The supply capillary 11 and the discharge capillary 12 are located at the distal end of the device 1 and form a special hydro-membrane nozzle 15. The front side of the outer supply capillary 11 is covered by a front ring 16, and the inner discharge capillary 12 is recessed lengthwise with respect to the outer supply capillary 11 by a predetermined amount. The difference a length between the supply capillary 11 and the discharge capillary 12 is greater than the wall thickness of the front ring 16, so that a radial annular throttle gap 17 is produced between the supply capillary 11 and the discharge capillary 12. For producing a desired throttle effect, the cross-sectional surface of the radial annular throttle gap 17 is smaller than the cross-sectional surface of the annular supply channel 14. The front ring 16 has a central nozzle opening 18, wherein the diameter of the nozzle opening 18 is matched within a predetermined tolerance range to the in a diameter of the discharge capillary 12.

The device 1 for removing an pathological center also includes a separate supply capillary 19. A pressure sensor 20 is arranged inside the supply capillary 19 and connected either to the supply line 7 of the hydraulic pump 8 or to the auxiliary unit 9. The supply capillary 19 is preferably rigidly connected to the outer supply capillary 11 or formed as a separate volume-compensating capillary. The length of the supply capillary 19 is identical to the length of the supply capillary 11.

For removing a clouded eye lens and replacing the clouded eye lens by an artificial lens, the eye is first incised in a conventional manner with a tunnel incision. The front capsule is then opened using a flawless, preferably circular capsulorhexis. The supply capillary 11 for the pressurized flow generator 3 and the volume-compensating supply capillary 18 of the device 1 is pushed into the diseased lens through this opening. Subsequently, the surgeon enables a hydraulic supply flow in the direction of the device 1 by activating the pressurized flow generator 3. The flow and pressure parameters of the pressurized flow generator 3 can be preset at the control unit 10. At the same time, the surgeon activates the reduced pressure flow generator 5 to produce a discharge flow at the preset flow and pressure settings and flowing in direction of the reduced pressure flow generator 5. As a result, a pressurized hydraulic flow passes from the pressure flow generator 3 through the supply line 2 into the annular supply channel 14, then passes through the radial annular throttle gap 17 and exits into free space. At this point, the hydraulic flow is entrained by the discharge flow of the reduced pressure flow generator 5 and transported through the discharge channel 13 of the discharge capillary 12 and the discharge line 4 in a retrograde direction to the reduced pressure flow generator 5. Different flow velocities between the supply flow and the discharge flow can be generated by suitably setting the flow and pressure parameters at the control unit 10 of the two flows. This produces a reduced pressure region at the hydro-membrane nozzle 15. The reduced pressure region generates at the mouth of the inner discharge capillary 12 a conical hydro-membrane which produces attracting forces acting on the immediate surroundings of the hydro-membrane nozzle 15. The strength of these attracting forces can be set and adjusted at the control unit 10.

The attracting forces dislodge the diseased tissue of the eye lens from the healthy tissue of the neighboring parts of the eye and, at the same time, comminute the dislodged lens fragments and transport the dislodged lens fragments to the mouth of the hydro-membrane nozzle 15. Smaller lens residues enter the discharge channel 13 unimpededly, whereas larger lens fragments impinge on the front ring 16 of the outer supply capillary 11, where they are further comminuted to a size suitable to be transported. The removal action produced by the attracting forces can be amplified by pulsating the supply flow through activation of the pulse generator 6.

To compensate for the volume loss within the lens chamber, the hydro-pump 8 is activated for supplying the eye chamber with a quantity of fluid that is equivalent to the volume of the diseased lens tissue which has been removed. This volume compensation can be performed continuously using the pressure sensor 20 or can be controlled manually. Alternatively, the volume can be compensated, for example, by using an auxiliary unit 9 in the form of a water jet device which produces a water jet flowing through the supply capillary 19 or a laser beam to perform additional measures in conjunction with the surgical procedure.

Advantageously, a heating device 21 may be embedded in the supply line 2 for suitably adjusting the temperature of the hydraulic flow.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. A device for removing a pathological center in humans and animals, comprising an axial supply capillary disposed around a coaxial discharge capillary;

a supply channel formed between the supply capillary and the discharge capillary;

a discharge channel formed by the discharge capillary;

the discharge capillary having an unobstructed opening at a distal end;

an annular front ring placed at the distal end of the supply capillary, defining an opening between the supply capillary and the discharge capillary and forming a radial annular throttle gap between the supply capillary and the discharge capillary;

wherein pressurized fluid is passed from a proximal end through the supply channel, passed the annular front ring through the opening of the supply capillary, and returns through the discharge channel.

2. A device for removing a pathological center in humans and animals, comprising a supply capillary and a supply channel for a pressurized flow and a discharge capillary with a discharge channel, which is open to the pathological center, for a suction flow;

the supply channel of the supply capillary includes a throttle located at the proximal distal end of the supply channel and is operatively connected with the discharge channel of the discharge capillary, wherein the supply capillary is formed as an outer capillary and the discharge capillary is formed as an inner capillary, both of which are pushed into each other coaxially on a common axis so as to form an annular gap therebetween, wherein the annular gap is formed as the supply channel, and the throttle is formed at the distal end of the device as a radial annular throttle gap and empties into the discharge channel of the discharge capillary, and wherein the radial annular throttle gap is formed by a lengthwise recessed end of the inner discharge capillary and by a front ring placed on the outer supply capillary.

3. The device according to claim 2, wherein the front ring comprises a nozzle opening having a diameter which is adapted to the diameter of the discharge channel.

4. The device according to claim 3, wherein the supply capillary is connected to an additional supply capillary extending parallel to the supply capillary.

5. The device according to claim 4, further comprising a pressure sensor arranged in the additional supply capillary.

* * * * *